United States Patent [19]

Visser et al.

[11] Patent Number: 6,033,844

[45] Date of Patent: *Mar. 7, 2000

[54] PORCINE REPRODUCTION RESPIRATORY SYNDROME DIAGNOSTIC

[75] Inventors: Nicolaas Visser, Boxmeer, Netherlands; Volker Ohlinger, Tubingen, Germany

[73] Assignee: Akzo Nobel, N.V., Arnhem, Netherlands

[ * ] Notice: This patent issued on a continued prosecution application filed under 37 CFR 1.53(d), and is subject to the twenty year patent term provisions of 35 U.S.C. 154(a)(2).

[21] Appl. No.: 08/863,116

[22] Filed: May 27, 1997

Related U.S. Application Data

[63] Continuation of application No. 08/211,776, filed as application No. PCT/EP92/02331, Oct. 9, 1992, abandoned.

[30] Foreign Application Priority Data

Oct. 14, 1991 [EP] European Pat. Off. .............. 91202646

[51] Int. Cl.⁷ ............................. C12Q 1/70; C12N 7/00; C07K 14/005; A61K 39/12
[52] U.S. Cl. .......................... 435/5; 435/235.1; 530/350; 424/204.1; 436/518
[58] Field of Search ............................. 424/204.1, 202.1; 435/235.1, 5, 236, 238; 436/518; 530/350

[56] References Cited

U.S. PATENT DOCUMENTS

| | | | |
|---|---|---|---|
| 4,452,902 | 6/1984 | Gordon et al. | 436/506 |
| 5,476,778 | 12/1995 | Chladek et al. | 435/235.1 |
| 5,620,691 | 4/1997 | Wensvoort et al. | 424/184.1 |
| 5,698,203 | 12/1997 | Visser et al. | . |

OTHER PUBLICATIONS

Bloemraad, M. et al. Veterinary Microbiology, vol. 42, p. 361–371, 1994.

Kim, H.S. et al. Archives of Virology, vol. 133, p. 477–483, 1993.

Freeman, Burrows Textbook of Microbiology, W.B.Saunders Co. Philadelphia, 1985, pp. 308–310.

G. Wensvoort et al., "Mystery Swine Disease in the Netherlands: The Isolation of Lelystad Virus", *The Veterinary Quarterly*, vol. 13, No. 3, pp. 121–130.

C. Terpstra et al., "Experimental Reproduction of Porcine Epidemic Abortion and Respiratory Syndrome (Mystery Swine Disease) by Infection with Lelystad Virus: Koch's Postulates Fulfilled", *The Veterinary Quarterly*, vol. 13, No. 3, Jul. 1991, pp. 131–136.

J.M.A. Pol et al., "Pathological, Ultrastructural, and Immunohistochemical Changes Caused by Lelystad Virus in Experimentally Induced Infections of Mystery Swine Disease (Synonym: Porcine Epidemic Abortion and Respiratory Syndrome (Pears))", *The Veterinary Quarterly*, vol. 13, No. 3, pp. 137–143.

G. Wensvoort et al. "'Blue Ear' Disease of Pigs", *The Veterinary Record*, vol. 128, No. 24, Jun. 15, 1991, London GB, p. 574.

McCullough et al., *The New Pig Disease*, pp. 46–52, Brussels, Apr. 29–30, 1991.

Wensvoort et al., *Veterinary Microbiology*, 33:185–193, 1992.

*Primary Examiner*—Mary E. Mosher
*Attorney, Agent, or Firm*—Mary E. Gormley

[57] ABSTRACT

The present invention is directed to the identification of the causative agent of Porcine Reproductive Respiratory Syndrome virus and vaccines derived therefrom. The present invention is also directed to viral antigens produced by tissue culture cells infected with this virus, and the use of such antigens in diagnostics.

8 Claims, 1 Drawing Sheet

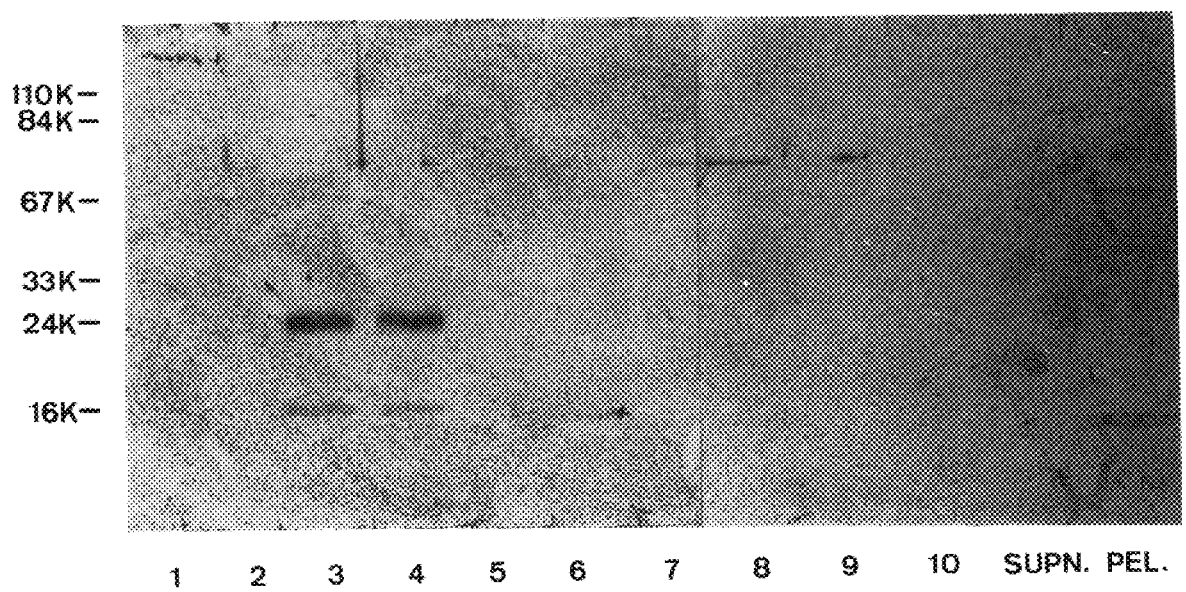

PORCINE REPRODUCTION RESPIRATORY SYNDROME DIAGNOSTIC

This is a continuation of application Ser. No. 08/211,776, filed as application No. PCT/EP92/02331, Oct. 9, 1992, now abandoned.

FIELD OF THE INVENTION

The present invention is concerned with a vaccine for the protection of pigs against Porcine Reproductive Respiratory Syndrome (PRRS), a biological composition comprising viruses of a novel virus type, a method for the preparation of viral antigen derived from viruses of this novel virus type, a method for the detection of antibodies to PRRS-virus, as well as a diagnostic test kit to be used in this method.

BACKGROUND OF THE INVENTION

A new porcine disease has attacked over 5,000 North European pig farms since late 1990. This disease is now called Porcine Reproductive Respiratory Syndrome (PRRS). First identified in Germany in December of 1990, the problem became increasingly critical in the beginning of 1991. In January and February of 1991 the disease spread to The Netherlands and Belgium. Outbreaks have also been reported from Spain.

It is anticipated that the disease will become very costly from an economic standpoint, comparable or even worse than Aujeszky's Disease.

The principal clinical signs in sows are anorexia and late abortion up to day 110 of pregnancy. With piglets a high incidence of stillborn weak piglets in addition to respiratory problems are observed. In fatteners chronic pneumonia and increased mortality occurs.

In order to develop a vaccine to protect pigs against PRRS or to develop a diagnostic method to determine infection in pigs, the causative agent of this disease has to be identified. However, up to now only a few characteristics of the causative agent have been disclosed, such as its viral nature, haemagglutination properties, buoyant density and growth characteristics in vitro (Wensvoort, G. et al., Vet. Quarterly 13, 121–130, 1991).

It is an object of the present invention to provide sufficient and unequivocally identifying characteristics of the new causative agent of PRRS necessary in order to prepare a vaccine and diagnostic test for the causative agent.

SUMMARY OF THE INVENTION

We now have identified a novel virus type, called PRRS virus, responsible for this disease, the novel virus type being characterized by the virus deposited at the CNCM under accession no. I-1140.

The virus of the new type can be isolated from lung tissues of clinical cases of PRRS. A 24-hour monolayer of alveolar macrophages was incubated with a 50% homogenate of lung tissue in phosphate buffered saline (PBS). The macrophage cell culture was established from lung lavages of SPF piglets with PBS. The macrophages were washed and incubated with RPM 1640 medium supplemented with 10% fetal calf serum and antibiotics for 24 hours in 5% $CO_2$ incubator. A small volume of the homogenate is added to the macrophages, after incubation for 1 h. at 37° C. new medium was added again and the infected macrophages were further incubated at 37° C. in $CO_2$ atmosphere. Total cytopathic effect (CPE) is apparent after 2–3 days of incubation.

The virus can also be isolated from other sources such as heart, tonsils, brain and liver of infected pigs.

The selected tissue homogenates of a clinical case of PRRS used for the isolation of the novel PRRS virus did not show consistently signs of the presence of other viral agents commonly found with pigs, especially not pseudorabies virus (PRV), porcine parvovirus (PPV), paramyxovirus, hog cholera virus (HCV) and transmissable gastroenteritis virus.

Other characteristic features of the novel PRRS virus are outlined below:

Virus Deposit

The novel PRRS virus specifically isolated as described above was accorded the internal description "Isolate no. 10" and has been deposited Sep. 6, 1991 with the Collection Nationale de Cultures de Micro-organismes (CNCM) of the Institut Pasteur at Paris, France under the accession number I-1140.

Growth Characteristics

The novel virus grows on macrophages but does not grow to measurable levels in the established cell lines BHK21, Vero, SK-6 (swine kidney), PK15 (porcine kidney), ST (swine testis), L929 and BEL (bovine embryo lung).

Serological Exclusion of Known Agents.

Using established techniques it was excluded that one of the following agents was the causative agent of PRRS.

| | test methods | | | |
|---|---|---|---|---|
| agent | VN[a] | gI Elisa[b] | HI[c] | IFT[d] |
| pseudorabies virus | — | — | N.D. | N.D. |
| porcine parvovirus | — | N.D. | — | N.D. |
| porcine paramyxovirus | — | N.D. | — | N.D. |
| porcine circovirus | N.D. | N.D. | N.D. | — |
| chlamydia | N.D. | N.D. | N.D. | — |

N.D. = not determined
[a]= virus neutralization test (VN) as described in Virologische Arbeitsmethoden Vol. 2, Eds.: A. Mayr et al., Fisher Verlag Jena, 1977, p. 457–535;
[b]= gI Elisa test as described in manual provided with Intertest Aujeszky gI Elisa kit;
[c]= haemagglutination inhibition test (HI) Virology, a practical approach, Ed.: B. W. J. Magy, IRL Press Oxford. 85, p. 245–248;
[d]= immunofluorescence test; Virologische Praxis, Ed.: G. Starke, Fischer Verlag Jena, 1968, p. 227–241.

Serological Correlation of the Infectious Agent with PRRS.

Field serum samples obtained from clinical cases were tested in an immunofluorescence test (IFT) using infected macrophages.

Further serum samples from pigs experimentally infected with the new virus were tested.

Microtitre plates seeded with Alveolar macrophages ($4 \times 10^4$ per well) were infected using Isolate No. 10 and incubated for 24 hours. At this time first signs of CPE appear. The cells are fixed with cold 96% ethanol (30 min.). Serial dilutions starting from $\frac{1}{10}$ of the serum samples were incubated on the fixed infected macrophages for 1 hour at 37° C. The second incubation was with rabbit anti-pig IgG conjugated to FITC (Nordic, Breda) ($\frac{1}{40}$ dil., 30 min., 37° C.). With an inverted Leitz immunofluorescence microscope specific fluorescence was determined. Specific fluorescence is characterized by sickle shaped perinuclear fluorescence.

In the Table below a comparison of a test set of sera is given.

| serum | IFT |
|---|---|
| 1. Experimental infection preserum | – |
| 2. Experimental infection one month post-infection | + |
| 3. Field serum 1 | + |

-continued

| serum | IFT |
| --- | --- |
| 4. Field serum 2 | + |
| 5. Field serum 3 | + |
| 6. Field serum 4 | + |
| 7. Field serum 5 | + |

Cross-reaction Between PRRS Isolates.

Although the PRRS virus is not antigenically related to known porcine viruses it could be demonstrated that different isolates of PRRS viruses are antigenically similar as they immunologically cross-react in the IF test.

The table below demonstrates that PRRS positive serum reacts with the various PRRS isolates in the IFT. Thus, any PRRS virus isolate can be used in the present invention because of their strong antigenic relationship as demonstrated with the IFT.

| isolate | IFT pos. serum |
| --- | --- |
| Intervet 10 | +++ |
| Intervet 2 | + |
| Intervet 3 | ++ |
| Intervet 4 | ++ |
| Geld B. 2 | +++ |
| Geld B. 3 | ++ |

Other Characteristics

The PRRS virus is an enveloped virus (sensitive to chloroform and ether treatment) with small knots on the surface and is similar to Lactate Dehydrogenase Virus and Equine Arteritis Virus. The virus particle is about 65 nm and has a buoyant density of 1.1 g/cm$^3$. In macrophage cell culture infected with the virus at least two virus-specific proteins can be detected of about 14,000 and 21,000 (Da).

BRIEF DESCRIPTION OF THE DRAWINGS

FIG. 1 is a Western blot of PRRS viral antigens that have been electrophoretically resolved and reacted with PRSS antisera.

DETAILED DESCRIPTION OF THE INVENTION

In accordance with the present invention, a vaccine is provided for the protection of pigs against PRRS, comprising viral antigen derived from viruses of a novel virus type characterized by the virus deposited at CNCM under accession No. I-1140.

From the above it is clear that the present vaccine can be prepared from both the Isolate no. 10 deposited with the CNCM under no. I-1140 and from any other available or isolatable PRRS virus isolates.

Preferably, a vaccine is provided using as viral antigen PRRS virus which is at least partly deprived of its pathogenic properties without losing its antigenic activity, i.e. the ability to stimulate the porcine immune system. This may be effected by attenuation or by inactivation of the virus in which latter case the virus also loses its ability to multiply.

In particular, the present invention provides an inactivated vaccine comprising one or more isolates of the novel virus in an inactivated form.

Preferably, the inactivated vaccine according to the invention comprises an amount of PRRS virus which is the equivalent of a pre-inactivation virus titre of greater than about $10^{6.5}$ TCID$_{50}$/ml (dose) and more preferably greater than about $10^{7.5}$ TCID$_{50}$/ml (dose) as measured with the method described in A. Mayr et al. (Eds.), Virologische Arbeitsmethoden Vol. 1, Fischer Verlag Jena, 1974, p. 36–39.

Inactivated PRRS fluids may also be concentrated by any number of available techniques such as an Amicon concentrating device, precipitation techniques such as with ammonium chloride or polyethylene glycol, concentration with Carbowax® or by means of ultra-centrifugation, or adjuvant concentration techniques such as with aluminium phosphate.

The aim of inactivation of the PRRS viruses is to eliminate reproduction of the viruses. In general, this can be achieved by chemical or physical means. Chemical inactivation can be effected by treating the viruses with, for example, formaldehyde, β-propiolactone, ethylene-imine or a derivative thereof, an organic solvent (such as Tween®, Triton X®, sodium desoxycholate, sulphobetain or octyl trimethylammonium salts). If necessary, the inactivating compound is neutralized afterwards; material inactivated with formaldehyde can, for example, be neutralized with metabisulphite. Physical inactivation can preferably be carried out by subjecting the viruses to energy-rich radiation, such as UV light, X-radiation or γ-radiation. If desired, the pH can be brought back to a value of about 7 after treatment.

Usually, an adjuvant and if desired one or more emulsifiers such as Tween® and Span® are also incorporated into the inactivated vaccine. Suitable adjuvants are for example vitamin-E acetate o/w emulsion, aluminium hydroxide, -phosphate or -oxide, (mineral) oil emulsions such as Bayol® and Marcol 52® and saponins.

For the production of the live attenuated virus vaccine according to the invention, a number of methods known in the art for this purpose are available, e.g. adaption of a specific PRRS virus isolate to growth in embryonated eggs or to a culture containing susceptible porcine tissue cells or other susceptible tissue cells, and attenuation for example by 10–200 passages in eggs or such cultures, after which the virus is multiplied and harvested by collecting egg material or the tissue cell culture fluids and/or cells. Optionally, during harvesting the yield of the viruses can be promoted by techniques which improve the liberation of the infective particles from the growth substrate, e.g. sonication.

It is advantageous to add a stabilizer to the live viruses, particularly if a dry composition is prepared by lyophilization. Suitable stabilizers are, for example, SPGA (Bovarnik et al., J. Bacteriology 59, 509, 1950), carbohydrates (such as sorbitol, mannitol, trehalose, starch, sucrose, dextran or glucose), proteins (such as albumin or casein), or degradation products thereof, and buffers (such as alkali metal phosphates). If desired, one or more compounds with adjuvant activity as described above can also be added.

For live vaccines the dose rate may range from $10^{1.0}$–$10^{7.0}$ TCID$_{50}$ per pig.

A vaccine according to the invention may be administered by intramuscular or subcutaneous injection or via intranasal, intratracheal, oral, cutaneous, percutaneous or intracutaneous administration.

The vaccine according to the invention can be administered to pigs depending on the vaccination history of the sows at 1, 5 or 10 weeks of age, to sows before mating and/or 4–6 weeks before farrowing (booster vaccination), or to boars each half a year (boosters).

Vaccines according to the present invention, preferably the vaccines containing inactivated PRRS viruses may contain combinations of the PRRS component and one or more unrelated porcine pathogens, such as Actinobacillus pleuropneumonia, Pseudorabies virus, Porcine influenza virus, Porcine parvovirus, Transmissible gastro-enteritis virus, rotavirus, *E. coli, Erysipelo rhusiopathiae, Pasteurella multocida, Bordetella bronchiseptica.*

Although a vaccine according to the invention may be derived from any PRRS virus isolate, preferably, the vaccine is derived from PRRS Isolate no. 10, CNCM accession no. I-1140.

A method for the preparation of PRRS viral antigen useful to be incorporated into a vaccine according to the invention includes the steps of a) inoculating susceptible tissue culture cells with the PRRS virus, b) cultivating the cells, and c) harvesting the viral antigen from the culture.

Preferably, the PRRS virus is cultured to high titres, i.e. at least $10^{6.0}$ TCID$_{50}$/ml.

In particular, the PRRS virus Isolate no. 10, CNCM accession no. I-1140 is used for the preparation high amounts of PRRS viral antigen.

Viral antigen to be incorporated into a vaccine according to the invention can be prepared by the growth of the PRRS virus isolates on macrophages (alveolar, peritoneal, peripheral, bone marrow or from any other site). Also other cells with macrophage-like properties are useful, like promonocytes, monocytes, brain vascular endothelial cells and microglial cells. The macrophage or macrophage-like cells may be of spf or non-spf origin (e.g. from regular commercial pigs). In the latter cases precautions are taken for undesired contamination, e.g. by the use of proper antibiotics in the culture.

Another set of routes which can lead to a very useful procedure of virus growth is the establishment of a macrophage cell line. A number of possibilities which can lead to such desirable macrophage cell lines are outlined below.

Immortalisation of macrophages using conditioned medium of L(929) cells, SK6, ST, Vero or BHK cells. In these conditioned media at least the presence of lymphokines like the macrophage Colony Stimulating Factor (CSF) is of importance (Stanley, E. R., Methods Enzymology 116, 564–587, 1985).

Treatment of macrophages of any source with chemicals to invoke immortalization, e.g. β-propiolactone as an example of an alkylating agent that effects DNA metabolism can be used (Logrippo, G. A. and Harman, F. W., J. Immunol. 75, 123–128, 1955).

A more defined way of immortalisation is the use of transforming viruses. Not limited to but especially retroviruses (e.g. leukemia virus), SV40 and Papilloma viruses are thus far described to immortalise macrophages of other species like man and mouse. (Robinson, D. H. et al., Blood 77, 294–305, 1991; Righi, M. et al., Oncogene 6, 103–111, 1991; Choi, C. S. et al., Arch. Virol. 115, 227–237, 1990; Gendelman, H. E. et al., Lab. Invert. 51, 547–555, 1984; ATCC catalogue for available mouse and human macrophage lines).

An even more precise way of immortalisation is the use of the genes of any of above mentioned or other viruses that are responsible for the immortalisation, for example Vmyc or Vmfs genes and/or the large T gene of SV40 may be used. The construction of a retroviral vector that allows the integration of a transforming gene like SV40 large T into the genome of the host cell would be the most preferable solution in that immortalisation is obtained without the actual replication and excretion of viral or viral-like particles. Also a plasmid containing a selectable marker (e.g. Neo®) and the SV40 large T gene would be a method for immortalisation.

As a source for immortalisation mature macrophages can be taken, however, very useful are also the cell stages before the differentiation to the mature macrophages because these are dividing cells with macrophage characteristics, and have macrophage markers as CD1, CD11 and CD14. The prestages can be selected and obtained in pure form free from contamination by other lymphocytes using various separating techniques for instance cell sorting with a FACS (Fluorescence Activated Cell Sorter) and fluorochrome labeled specific antibodies against the CD markers.

The demand for sensitive, specific methods for screening and identifying carriers of PRRS virus is significant.

Therefore, the present invention is also directed to a rapid and sensitive assay for the detection of antibodies to PRRS virus.

It is a further object of the invention to provide diagnostic test kits for performing the assay method of the invention.

According to the present invention a method for the detection of antibodies to PRRS virus is provided comprising:

a) incubating a sample suspected of containing anti-PRRS virus antibodies with PRRS viral antigen reagent derived from viruses of a novel virus type characterized by the virus deposited at the CNCM under accession no. I-1140, under conditions which allow the formation of an antibody-antigen complex, and b) detecting the antibody-antigen complex.

The viral antigen from PRRS infected cells which react immunologically with serum containing anti-PRRS virus antibodies are useful as reagent in immunoassays to detect presence of PRRS virus antibodies in biological samples. The viral antigen reagent can be, inter alia, purified or partially purified virus particles or viral polypeptides, disrupted virus or infected cells or cell lysate therefrom.

The design of the immunoassay may vary. For example, the immunoassay may be based upon competition or direct reaction, or sandwich type assays. Furthermore, protocols may use solid supports or may be by immuno-precipitation. The detection of the antibody-antigen complex may involve the use of labeled antibody; the labels may be, for example fluorescent, chemiluminescent, radioactive, dye molecules or enzyme labels.

Present methods useful for the detection of antibodies to PRRS virus include the enzyme-linked immuno-sorbent assay (ELISA), immunofluorescence test (IFT) and Western Blot technique.

The ELISA technique involves the reacting of a test sample with viral antigen reagent obtained from PRRS virus. Preferably, the antigen reagent is a cell lysate of macrophages infected with PRRS virus. Typically, the antigen reagent is coated onto a solid phase, e.g. a microplate or plastic cup. After washing to remove the unbound antibodies anti-immunoglobulin labeled with enzyme is added to the solid phase, incubated, and washed again. Enzymes suitable for labeling are known in the art and include for example horseradish peroxidase. Thereafter, an enzyme substrate is added to the mixture and a detectable, measurable color product is formed in the presence of antibodies to PRRS virus.

In addition, the IFT technique can be used according to the present invention. For example, macrophages infected with PRRS virus are cultured in microtitre plates for 24 hours. Thereafter the cells are fixed with for example acetone or ethanol or by freeze-thawing in combination with formalin treatment. The test sample is then added to the fixed cells and incubated for 1 h. at 37° C. Subsequently, anti-immunoglobulin conjugated with a fluorescent compound such as fluorescein is added to the fixed cells. Reaction mixtures are then examined for fluorescence under a microscope. A typical fluorescence pattern of PRRS virus infected macrophages incubated with a positive serum of a pig infected with PRRS can be demonstrated.

The preferred diagnostic method according to the invention is directed to the detection of PRRS antibodies using the Western Blot technique.

In this technique PRRS viral antigen is electrophoretically resolved on SDS-polyacrylamide gels. Preferably, the viral antigen is the cell lysate of PRRS virus infected macrophages. The resulting protein bands are electrotransfered, preferably to nitrocellulose paper. Other types of paper, known to those skilled in the art, such as diazo paper are also suitable. (Tsang et al., In: Methods in Enzymology 92, chapter 29, 1983). The nitrocellulose strips containing the resolved viral antigen are then incubated with the test samples, and if desired with positive and negative reference samples. If desired negative reference strips, e.g. containing electrophoretically resolved macrophage lysate obtained from macrophages non-infected with PRRS virus are also incubated with the test sample. The positive reference sample is typically a sample known to contain antibodies to PRRS virus, e.g. serum from clinical cases of PRRS or from animals experimentally infected with PRRS virus. The negative reference sample is a sample known to be devoid of antibodies to PRRS virus. Detection of the antibody-antigen complex may then be carried out by either ELISA or solid phase strip radio-immunoassay techniques. Washings may be carried out after each incubation.

Preferably, the incubation of the strips is carried out in containers.

Surprisingly, the Western Blot technique is particularly suitable for the detection of PRRS virus specific polypeptides obtained from an in vitro cell culture because of the presence of two or three small virus specific proteins separately identifiable from other material reactive with PRRS serum. As is shown in FIG. 1 the major immune reactivity or specificity is directed against an about 14,000 and 21,000 (Da) protein of the PRRS virus (Western blot of glycerol gradient purified PRRS virus cultured on macrophages). The 21,000 (Da) band is diffuse and therefore the designation 21,000 (Da) is only meant as an indication of the size of this protein.

Other virus specific proteins recognized by antibodies to PRRS virus in Western blot have molecular weights of about 46,000, 49,000 and 55,000 (Da).

With purified $^{35}$S-Met/Cys labeled virions, 14K, 24K, 33K and 46K proteins were shown to be prominent. Radio-immunoprecipitation of $^{35}$S-Met/Cys labeled infected cell lysates resulted in demonstration of two virus-specific proteins of about 24K and 33K. The above-noted virus specific proteins can also be used for the diagnosis of PRRS infection.

In a preferred embodiment of the invention the purified 14,000 and 21,000 (Da) PRRS virus orotein may be used in the ELISA and Western Blot technique as the viral antigen reagent in order to provide a more sensitive assay.

In accordance with an other embodiment of the invention, a diagnostic test kit is provided which permits "on site" screening for antibodies to PRRS virus. The test kit includes at least one strip containing resolved PRRS viral antigen, (electro-) transfered from a SDS-PAGE gel. in addition the kit may comprise a negative control reference strip, e.g. containing resolved antigen from an in vitro cell culture, e.g. macrophage cell culture, not-infected with PRRS virus.

Preferably, the strips are contained in individual containers facilitating the subsequent incubation steps.

Furthermore, it is advantageous to include in the test kit the positive and negative reference samples in order to facilitate evaluation of the test results by comparison with the results obtained for the test sample.

If desired pre-developed positive and negative reference strips are also provided in the kit. The pre-developed strips are used to evaluate the test results by a visual comparison with the test strips after condition of a color reaction. The pre-developed strips facilitate reading the assay results and practically eliminate the need for a skilled technician to evaluate the results. Included in the kit may also be vials of enzyme-conjugated antiserum reagent, preferably horseradish peroxidase conjugated immunoglobulins, substrate or color change indicator, washing buffers and solution for terminating the color reaction. The preferred substrate, reaction terminating agent and washing buffers are DAB, distilled water and PBS Tween® and PBS, respectively.

In a most preferred embodiment of this test kit the about 14,000 and 21,000 (Da) protein bands of the PRRS virus test strips containing the resolved PRRS viral antigen are separately identifiable, i.e. these bands are separated from other viral or non-viral antigens reactive with the PRRS serum.

To measure PRRS viral antigen in a test sample, known PRRS specific antiserum or antibodies are used as a reagent, preferably fixed to a solid phase. The test sample containing antigen is added, and after incubation allowing the formation of an antigen-antibody complex, the solid phase is washed, and a second labeled antibody is added to detect the antigen-antibody complex.

Furthermore, the present invention is directed to test kits to be used in accordance with the method for the detection of PRRS viral antigen in a test sample as described above.

EXAMPLE 1

Isolation and Propagation of PRRS Virus

SPF piglets kept in isolation facilities are aneasthesised and lung lavage is performed using warm phosphate-buffered saline (PBS). About 100 ml of macrophages suspension is collected in siliconised glass bottles. The macrophaqes are washed with PBS and incubated with RPM 1640 medium (Flow Labs) supplemented with 10% fetal calf serum and antibiotics for 24 hours in 5% $CO_2$—incubator. The cells were seeded in 25 $cm^2$ Roux flasks (Falcon) at a density of $3 \times 10^5$ per $cm^2$.

Sow 266 suffering from clinical symptoms of PRRS (abortion, off feed) diagnosed by a veterinarian of the Regional Animal Health Institute was taken for post mortem.

A 50% homogenate of lung tissue in PBS was prepared using an Ultraturrax®. Low speed centrifugation was used to clarify the suspension. One ml of the clarified supernatant was taken and inoculated onto a 24-hour monolayer of alveolar macrophages. After incubation for 1 h at 37° C the medium was added again and the infected macrophages were further incubated at 37° C. in $CO_2$ atmosphere. After 2 days first signs of CPE became apparent. At day 3 the macrophages showed complete lysis, which was confirmed by the uptake of trypan blue.

Viable cells do exclude trypan blue dye, as did the non-infected control macrophages. The harvest of this first passage was stored at −70° C. Further passages of this isolate were made by incubation of 1 ml prediluted 1:10–1:100 virus on further macrophages cultures. Total CPE is apparent after 2–3 days of incubation. This PRRS isolate was accorded the internal code "Isolate No. 10". A sample of this isolate has been deposited with the CNCM under accession No. I-1140.

The method for the preparation of PRRS viral antigen as described above results in the ability to grow the virus to high titres in vitro. Table 1 shows the results of the virus yield after several passage levels of Isolate No. 10.

TABLE 1

| Growth characteristics in macrophages | |
|---|---|
| passage level | Titer ($TCID_{50}$/ml) |
| 3 | $10^{6.0}$ |
| 4 | $10^{6.0}$ |
| 5 | $10^{7.0}$ |
| 6 | $10^{6.7}$ |
| 7 | $10^{7.4}$ |
| 8 | $10^{7.5}$ |

EXAMPLE 2

Experimental Infection of PRRS Virus in Four-week-old Pigs

Isolate No. 10 ($10^{5.0}$ $TCID_{50}$) was inoculated intranasally into two four-week-old pigs housed in one pen with a contact control. Clinically in the animals anorexia was observed for four days and a slight transient temperature rise. Further for 6 days they were duff and slow. 8 Days p.i. the two infected animals were anesthetised and lung lavages were performed. In one of those pigs the causative agent was reisolated upon co-cultivation with spf macrophages.

Furthermore seroconversion was measured in both the infected pigs as well as in the contact control.

Seroconversion was measured in the Immuno-Fluorescent Assay (IFA). Monolayers of macrophages 24 hours after infection with Isolate 10 were fixed with 95% −70° C. ethanol for 1 hour and incubated with the test sera for 1 hour 37° C. FITC-conjugated rabbit anti-swine IgG was added and incubated for 30 min at 37° C. The samples were read using an UV-fluorescent microscope (Leitz). 4 weeks after vaccination antibody titer in the vaccinates was more than 1280.

EXAMPLE 3

Vaccination of Pregnant Sows

5 Sows 10 weeks from time of farrowing were housed in containment facilities. 3 Sows are vaccinated i.m. (pre-inactivation titer $10^{7.2}$ $TCID_{50}$/ml) in the neck with inactivated isolate No. 10 adjuvanted in a water-in-oil (Freund incomplete) emulsion (1 ml) and boostered 4 weeks later. At day 80 of gestation, about 3 weeks before delivery, the vaccinates and controls are challenged infected intranasally with Isolate No. 10 ($10^{5.0}$ $TCID_{50}$).

The serological response in the sows is monitored.

The challenge of the vaccinated sows before farrowing revealed a protection. The vaccinated sows had significantly more healthy piglets than the controls (Table 2). The table shows the effect of the challenge on the progeny of vaccinated and control sows at the time of birth and for the live born during the first week after birth.

TABLE 2

| | Piglets born[a] | | Neonatal piglets[a] | | |
|---|---|---|---|---|---|
| Treatment | Mummies | Deaths | Deaths | Weak | Healthy |
| Vaccinated | 1.7 | 2 | 1.7 | 0.7 | 6.7 |
| Controls | 1 | 3 | 3 | 2 | 2 |

[a]mean number of piglets per sow.

EXAMPLE 4

Western Blot Immuno-assay

Supernatants from infected as well as uninfected macrophage cultures were clarified at 3,000 g. The supernatants were centrifuged in a SW 28.1 rotor at 25,000 rpm for 3 hours. The pellets were resuspended in TEN-buffer and used in gel electrophoresis.

The material was separated by electrophoresis under reducing conditions in a 10% sodium dodecyl sulfate (SDS)-polyacrylamide gel. The gels were equilibrated in renaturation buffer (4 M urea, 50 mM NaCl, 10 mM Tris hydrochloride, 0.1 mM dithiothreitol [pH 7]) for 30 min. and then incubated in electrophoresis buffer without SDS for an additional 30 min. Electrophoretic transfer to nitrocellulose membranes (Schleicher & Schuell, Dassel, FRG) was performed in a Mini Trans-Blot electrophoretic transfer cell (Bio-Rad, Munich, FRG) at 2 A for 1 h. Nonspecific binding of proteins to the membrane was blocked by incubation with dry milk powder solution in PBS for 2 h. PRRSV-positive pig antisera diluted in dry milk powder solution in PBS were allowed to bind overnight, and specific binding was detected using a goat anti-porcine peroxidase-conjugated antiserum (Dianova) and 2,2-chloronaphthol (Sigma) as the substrate.

We claim:

1. A method for the detection of antibodies to PRRS virus, comprising the steps of:

(a) incubating a test sample suspected of containing anti-PRRS virus antibodies with a composition containing at least one purified PRRS viral antigen selected from the group consisting of an about 14,000 dalton and an about 21,000 dalton PRRSV protein as determined by SDS-PAGE, under conditions that allow the formation of an antibody-antigen complex, and (b) detecting the antibody-antigen complex.

2. The method according to claim 1, wherein the antibody-antigen complex is detected by using a labeled antibody.

3. The method according to claim 2, wherein the label is an enzyme.

4. The method according to claim 3, wherein the method is an ELISA.

5. The method according to claim 1, wherein the antigen is bound to a solid support.

6. The method according to claim 5, wherein the method comprises a Western Blot technique.

7. A diagnostic test kit for detection of antibodies to PRRS virus, comprising at least one purified PRRS viral antigen selected from the group consisting of an about 14,000 dalton and an about 21,000 dalton PRRSV protein as determined by SDS-PAGE.

8. A purified PRRS viral antigen selected from the group consisting of an about 14,000 dalton and an about 21,000 dalton PRRSV protein as determined by SDS-PAGE.

* * * * *